US010772963B2

(12) United States Patent
Manning et al.

(10) Patent No.: US 10,772,963 B2
(45) Date of Patent: *Sep. 15, 2020

(54) ETANERCEPT FORMULATIONS STABILIZED WITH XYLITOL

(71) Applicant: Coherus Biosciences, Inc., Redwood City, CA (US)

(72) Inventors: Mark Manning, Johnstown, CO (US); Brian Murphy, Fort Collins, CO (US)

(73) Assignee: Coherus Biosciences, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/284,265

(22) Filed: Feb. 25, 2019

(65) Prior Publication Data

US 2019/0184017 A1    Jun. 20, 2019

Related U.S. Application Data

(60) Continuation of application No. 15/716,005, filed on Sep. 26, 2017, now Pat. No. 10,213,508, which is a continuation of application No. 15/209,484, filed on Jul. 13, 2016, now Pat. No. 9,770,510, which is a division of application No. 13/654,919, filed on Oct. 18, 2012, now Pat. No. 9,393,305.

(60) Provisional application No. 61/669,480, filed on Jul. 9, 2012, provisional application No. 61/548,518, filed on Oct. 18, 2011.

(51) Int. Cl.
| | |
|---|---|
| *C07K 14/705* | (2006.01) |
| *A61K 38/17* | (2006.01) |
| *A61K 47/10* | (2017.01) |
| *A61K 47/26* | (2006.01) |
| *A61K 39/395* | (2006.01) |
| *A61K 9/16* | (2006.01) |
| *C07K 14/715* | (2006.01) |
| *A61K 38/19* | (2006.01) |
| *A61K 9/00* | (2006.01) |
| *A61K 9/08* | (2006.01) |
| *A61K 9/14* | (2006.01) |
| *A61K 47/18* | (2017.01) |
| *A61P 29/00* | (2006.01) |
| *A61P 19/02* | (2006.01) |
| *A61P 17/06* | (2006.01) |

(52) U.S. Cl.
CPC ............ *A61K 47/26* (2013.01); *A61K 9/0019* (2013.01); *A61K 9/08* (2013.01); *A61K 9/14* (2013.01); *A61K 9/16* (2013.01); *A61K 38/17* (2013.01); *A61K 38/1793* (2013.01); *A61K 38/191* (2013.01); *A61K 39/39591* (2013.01); *A61K 47/10* (2013.01); *A61K 47/18* (2013.01); *C07K 14/705* (2013.01); *C07K 14/7151* (2013.01); *A61P 17/06* (2018.01); *A61P 19/02* (2018.01); *A61P 29/00* (2018.01); *C07K 2319/30* (2013.01)

(58) Field of Classification Search
None
See application file for complete search history.

(56) References Cited

U.S. PATENT DOCUMENTS

| | | | |
|---|---|---|---|
| 5,580,856 | A | 12/1996 | Prestrelski et al. |
| 6,171,586 | B1 | 1/2001 | Lam et al. |
| 7,294,481 | B1 | 11/2007 | Fung |
| 7,648,702 | B2 | 1/2010 | Gombotz et al. |
| 7,915,225 | B2 | 3/2011 | Finck et al. |
| 8,758,747 | B2 | 6/2014 | Kallmeyer et al. |
| 9,302,002 | B2 | 4/2016 | Maning |
| 9,393,305 | B2 | 7/2016 | Manning |
| 9,770,510 | B2 | 9/2017 | Manning |
| 2003/0180287 | A1 | 9/2003 | Gombotz et al. |
| 2006/0177444 | A1 | 8/2006 | Horizoe |
| 2006/0292148 | A1 | 12/2006 | Matsumoto |
| 2007/0196364 | A1 | 8/2007 | Krishnamurthy et al. |
| 2007/0243185 | A1 | 10/2007 | Gombotz et al. |
| 2008/0108106 | A1 | 5/2008 | Wang et al. |
| 2008/0112953 | A1 | 5/2008 | Mcauley et al. |
| 2008/0124326 | A1 | 5/2008 | Rehder et al. |
| 2008/0213282 | A1 | 9/2008 | Jacob et al. |
| 2008/0311119 | A1 | 12/2008 | Maloney |
| 2009/0048122 | A1 | 2/2009 | Glaser et al. |
| 2009/0068705 | A1 | 3/2009 | Drapeau et al. |
| 2009/0117097 | A1 | 5/2009 | Igawa et al. |
| 2009/0163424 | A1 | 6/2009 | Finck et al. |
| 2009/0291062 | A1 | 11/2009 | Raunhofer et al. |
| 2010/0158908 | A1 | 6/2010 | Rehder et al. |
| 2010/0166774 | A1 | 7/2010 | Dali et al. |
| 2011/0091936 | A1 | 4/2011 | Gawlitzek et al. |
| 2011/0129468 | A1 | 6/2011 | Mccue et al. |

(Continued)

FOREIGN PATENT DOCUMENTS

| | | |
|---|---|---|
| CN | 1244805 A | 2/2000 |
| CN | 1829739 A | 9/2006 |

(Continued)

OTHER PUBLICATIONS

Kashanian S. et al., Effect of osmolytes on the conformational stability of mouse monoclonal antidigoxin antibody in long-term storage, Hybridoma (Larchmt), Apr. 2008, 27(2), 99-106.

(Continued)

*Primary Examiner* — Zachary C Howard
(74) *Attorney, Agent, or Firm* — Rothwell, Figg, Ernst & Manbeck, P.C.

(57) ABSTRACT

The invention provides stabilized aqueous pharmaceutical etanercept compositions suitable for long-term storage of etanercept, methods of manufacture of these compositions, methods of administration, and kits containing same.

15 Claims, No Drawings

(56) References Cited

U.S. PATENT DOCUMENTS

| | | | |
|---|---|---|---|
| 2012/0208986 | A1 | 8/2012 | Wenger et al. |
| 2013/0150554 | A1 | 6/2013 | Melville et al. |
| 2013/0224855 | A1 | 8/2013 | Gupta et al. |
| 2014/0199303 | A1 | 7/2014 | Choi et al. |
| 2014/0248274 | A1 | 9/2014 | Kallmeyer et al. |

FOREIGN PATENT DOCUMENTS

| | | | |
|---|---|---|---|
| CN | 101237890 | A | 8/2008 |
| CN | 101969971 | A | 2/2011 |
| CN | 102239177 | A | 11/2011 |
| CN | 103930124 | A | 7/2014 |
| EA | 201490195 | A1 | 4/2014 |
| EA | 201391739 | A1 | 5/2014 |
| EP | 1478394 | A2 | 11/2004 |
| EP | 1607103 | A1 | 12/2005 |
| EP | 1 908 482 | A1 | 4/2008 |
| ES | 2311094 | T3 | 2/2009 |
| JP | 2005527503 | A | 9/2005 |
| JP | 2009521482 | A | 6/2009 |
| JP | 2009534390 | A | 9/2009 |
| JP | 2010506911 | A | 3/2010 |
| JP | 2010513522 | A | 4/2010 |
| JP | 2010529999 | A | 9/2010 |
| JP | 2014518276 | A | 7/2014 |
| JP | 2014519484 | A | 8/2014 |
| JP | 2014522402 | A | 9/2014 |
| TW | 200510453 | A | 3/2005 |
| TW | 201311293 | A1 | 3/2013 |
| WO | 1998022136 | A2 | 3/1998 |
| WO | 0158473 | A1 | 8/2001 |
| WO | 2003/072060 | A2 | 9/2003 |
| WO | 2004075918 | A1 | 9/2004 |
| WO | 2005012353 | A1 | 2/2005 |
| WO | 2005/037214 | A2 | 4/2005 |
| WO | 2005/082377 | A1 | 9/2005 |
| WO | 2005/095578 | A1 | 10/2005 |
| WO | 2006/026447 | A2 | 3/2006 |
| WO | 2006132363 | A1 | 12/2006 |
| WO | 2007/076354 | A2 | 7/2007 |
| WO | 2007076062 | A2 | 7/2007 |
| WO | 2007124082 | A2 | 11/2007 |
| WO | 2008045373 | A2 | 4/2008 |
| WO | 2008051363 | A2 | 5/2008 |
| WO | 2008079290 | A2 | 7/2008 |
| WO | 2008/152075 | A1 | 12/2008 |
| WO | 2008157356 | A2 | 12/2008 |
| WO | 2009/111347 | A1 | 9/2009 |
| WO | 2011/015926 | A1 | 2/2011 |
| WO | 2011079308 | A1 | 6/2011 |
| WO | 2011/134920 | A1 | 11/2011 |
| WO | 2011141926 | A2 | 11/2011 |
| WO | 2012/013980 | A1 | 2/2012 |
| WO | 2012143418 | A1 | 10/2012 |
| WO | 2012165917 | A1 | 12/2012 |
| WO | 2013/006479 | A2 | 1/2013 |
| WO | 2013006454 | A1 | 1/2013 |

OTHER PUBLICATIONS

O'Donnell, J.O., Calcium phosphate precipitates legal problems for hospital and pharmacists, Pharmacy Practice News 2004, Jan. 2004, 31(1).

Mease et al., 2017, Therapeutics and Clinical Risk Management, 3 (1):133-148.

Carpenter et al., "Overlooking Subvisible Particles in Therapeutic Protein Products: Gaps that May Compromise Product Quality", Journal of Pharmaceutical Sciences, vol. 98, No. 4, Apr. 2009, pp. 1201-1205.

Hawe et al. "Taylor Dispersion Analysis Compound to Dynamic Light Scattering for the Size Analysis of Therapeutic Peptides and Proteins and Their Aggregates", Pharm Res (2011) 28: pp. 2302-2310.

Maggio, "Use of excipients to control aggregation in peptide and protein formulations", J. Excipients and Food Chem., 1 (2) 2010, pp. 40-49.

Tellez, CM, et al., Method for the characterization of size-exclusion chromatography media for preparative purification of DNA restriction fragments, Jun. 1999, Biotechnology Techniques, 13(6), 395-401.

Caporali R, et al., Diffuse skin reaction after changing the etanercept formulation, Nov. 1, 2008, Clinical and Experimental Rheumatology, 26(6), 1165.

EP Examination Report issued for EP14776207.4 dated May 27, 2016.

Niazi, SK. "Enbrel" Handbook of pharmaceutical manufacturing formulations: Sterile products, 2009, 410.

English language translation of Examination Report for corresponding Colombian Patent Application CO15076746 dated Oct. 9, 2017.

Gazerani, Pet al., Effects of subcutaneous administration of glutamate on pain, sensitization and vasomotor responses in healthy men and women, Pain, Oct. 2006, 124(3), 338-348.

Bolli, R. et al., L-Proline reduces IgG dimer content and enhances the stability of intravenous immunoglobulin (IVIG) solutions, Biologicals, Jan. 2010, 38(1), 150-157.

EP Examination Report issued for EP15742902.8 dated Jun. 9, 2017.

Falconer R.J., et al., Stabilization of a monoclonal antibody during purification and formulation by addition of basic amino acid excipients, J Chem Technol Biotechnol, 2011, 86, 942-948.

Chari, R., et al., Long- and short-range electrostatic interactions affect the rheology of highly concentrated antibody solutions, Pharm. Res., Dec. 2009, 26(12), 2607-2618.

Chaudhri A, et al., Coarse-grained modeling of the self-association of therapeutic monoclonal antibodies, J Phys Chem B, Jul. 19, 2012, 116(28), 8045-8057.

Chaudhri A. et al., The role of amino acid sequence in the self-association of therapeutic monoclonal antibodies insights from coarse-grained modeling, J Phys Chem B, Feb. 7, 2013, 117(5), 1269-1279.

EP Examination Report issued for EP15742902.8 dated Mar. 1, 2018.

Buck, P.M. et al., Highly viscous antibody solutions are a consequence of network formation caused by domain-domain electrostatic complementarities: insights from coarse-grained simulations, Mol Pharm, Jan. 5, 2015, 12(1), 127-139.

English language translation of Examination Report for corresponding Singapore Patent Application SG11201605860S dated May 24, 2017.

Bowers Randall et al., New Analytical Methods to Determine Calcined Coke Porosity, Shape, and Size, Light Met., vol. 2008, pp. 875-880, JSTPlus, [online], G-Search Limited., 2008, [Searched on Mar. 21, 2017], [Retrieve from: JDreamIII, internet: <URL:http://jdream3.com/>.

Heidemann, R. et al., The use of peptones as medium additives for the production of a recombinant therapeutic protein in high density perfusion cultures of mammalian cells, Cytotechnology, 2000, 32: 157-167.

Hossler, P. et al., Review: Optimal and consistent protein glycosylation in mammalian cell culture, Glycobiology, 2009, vol. 19, No. 9, pp. 936-949.

Altamirano, C. et al., Strategies for fed-batch cultivation of t-PA producing CHO cells: substitution of glucose and glutamine and rational design of culture medium, Journal of Biotechinology, 2004, 110: 171-179.

Bonarius, H. et al., Metabolic-Flux Analysis of Continuously Cultured Hybridoma Cells Using 13CO2 Mass Spectrometry in Combination with 13C-Lactate Nuclear magnetic Resonance Spectroscopy and Metabolite Balancing, Biotechnology and Bioengenieering, 2001, vol. 74, No. 6, pp. 528-538.

Reinhart D. et al, Benchmarking of commercially available CHO cell culture media for antibody production. BMC Proceedings, Dec. 4, 2013, vol. 7, No. Supp 6, pp. 13.

Examination Report for corresponding European Patent Application No. 12841765.6 dated Feb. 5, 2015.

(56) References Cited

OTHER PUBLICATIONS

Translation of Examination Report for corresponding Japanese Patent Application No. 2014537223 dated Jun. 21, 2016.
Examination Report for corresponding Singaporean Patent Application No. 11201401517V dated Sep. 21, 2015.
Translation of Search Report for corresponding Taiwanese Patent Application No. 101138564 dated May 26, 2016.
International Search Report and Written Opinion for corresponding PCT Application No. PCT/US2012/060739 dated Dec. 7, 2012.
International Search Report and Written Opinion for corresponding PCT Application No. PCT/US2012/060741 dated Jan. 18, 2013.
International Search Report and Written Opinion for corresponding PCT Application No. PCT/US2012/060743 dated Jan. 18, 2013.
International Search Report and Written Opinion for corresponding PCT Application No. PCT/US2012/060745 dated Jan. 18, 2013.
International Search Report and Written Opinion for corresponding PCT Application No. PCT/US2012/060748 dated Jan. 3, 2013.
Examination Report for corresponding Australian Patent Application No. 2012326168 dated Aug. 17, 2016.
Translation of Examination Report for corresponding Chinese Patent Application No. 201280062758.7 dated Jun. 30, 2015.
Translation of Examination Report for corresponding Eurasian Patent Application No. 201490815 dated Jun. 4, 2015.
Examination Report for corresponding European Patent Application No. 12842226.8 dated Jan. 28, 2015.
Translation of Examination Report for corresponding Israeli Patent Application No. 231824 dated Jun. 14, 2016.
Translation of Examination Report for corresponding Taiwanese Patent Application No. 101138561 dated Feb. 15, 2016.
Examination Report for corresponding Australian Patent Application No. 2012326170 dated Aug. 18, 2016.
Translation of Examination Report for corresponding Chinese Patent Application No. 201280062747.9 dated Jan. 27, 2015.
Translation of Examination Report for corresponding Chinese Patent Application No. 201280062747.9 dated Oct. 21, 2015.
Translation of Examination Report for corresponding Chinese Patent Application No. 201280062747.9 dated May 16, 2016.
Examination Report for corresponding European Patent Application No. 12842352.2 dated Jun. 8, 2015.
Translation of Examination Report for corresponding Japanese Patent Application No. 2014537219 dated Jul. 19, 2016.
Examination Report for corresponding Singaporean Patent Application No. 11201401563S dated Jan. 20, 2016.
Translation of Examination Report for corresponding Taiwanese Patent Application No. 101138565 dated May 24, 2016.
Examination Report for corresponding Australian Patent Application No. 2012326171 dated Aug. 22, 2016.
Translation of Examination Report for corresponding Chinese Patent Application No. 201280062748.3 dated Feb. 6, 2015.
Translation of Examination Report for corresponding Chinese Patent Application No. 201280062748.3 dated Dec. 3, 2015.
Translation of Examination Report for corresponding Eurasian Patent Application No. 201490804 dated May 25, 2015.
Translation of Examination Report for corresponding Eurasian Patent Application No. 201490804 dated Jan. 26, 2016.
Examination Report for corresponding European Patent Application No. 12841522.1 dated Jan. 28, 2015.
Translation of Examination Report for corresponding Japanese Patent Application No. 2014537220 dated Jun. 21, 2016.
Examination Report for corresponding Singaporean Patent Application No. 11201401562R dated Jan. 16, 2016.
English language translation of Examination Report for corresponding Chilean Patent Application CL0572-2015 dated Aug. 22, 2016.
Translation of Examination Report for corresponding Chinese Patent Application No. 201280062761.9 dated Apr. 3, 2015.
Translation of Examination Report for corresponding Chinese Patent Application No. 201280062761.9 dated Jan. 29, 2016.
Translation of Examination Report for corresponding Chinese Patent Application No. 201280062761.9 dated Jul. 21, 2016.
Translation of Examination Report for corresponding Eurasian Patent Application No. 201490802 dated May 14, 2015.
Translation of Examination Report for corresponding Eurasian Patent Application No. 201490802 dated Feb. 29, 2016.
Examination Report for corresponding European Patent Application No. 12841505.6 dated Jan. 28, 2015.
Translation of Examination Report for corresponding Japanese Patent Application No. 2014537221 dated Jun. 21, 2016.
Translation of Search Report for corresponding Taiwanese Patent Application No. 101138566 dated Mar. 1, 2016.
Examination Report for corresponding Australian Patent Application No. 2012326082 dated Aug. 16, 2016.
Translation of Examination Report for corresponding Chinese Patent Application No. 201280062739.4 dated Mar. 30, 2015.
International Search Report and Written Opinion for corresponding PCT application No. PCT/US2012/060738 dated Jan. 7, 2013.
Translation of Examination Report for corresponding Chinese Patent Application No. 201280062739.4 dated Jan. 29, 2016.
Translation of Examination Report for corresponding Eurasian Patent Application No. 201490803 dated Jun. 4, 2015.
Translation of Examination Report for corresponding Eurasian Patent Application No. 201490803 dated Feb. 12, 2016.
English language translation of Examination Report for corresponding Chinese Patent Application CN201380058650.5 dated Apr. 26, 2016.
Translation of Examination Report for corresponding Japanese Patent Application No. 2014537222 dated Jun. 21, 2016.
Translation of Search Report for corresponding Taiwanese Patent Application No. 101138567 dated Dec. 24, 2015.
Examination Report for corresponding Australian Patent Application No. 2012326084 dated Aug. 16, 2016.
Translation of Examination Report for corresponding Chinese Patent Application No. 201280062418.4 dated Jan. 30, 2015.
Translation of Examination Report for corresponding Chinese Patent Application No. 201280062418.4 dated Sep. 15, 2015.
Translation of Examination Report for corresponding Eurasian Patent Application No. 201490801 dated Jun. 4, 2015.
Translation of Examination Report for corresponding Eurasian Patent Application No. 201490801 dated Oct. 15, 2015.
English language translation of Examination Report for corresponding Japanese Patent Application No. 2014-537218 dated Jul. 26, 2016.
English language translation of Examination Report for corresponding Taiwanese Patent Application No. 101138560 dated Jun. 23, 2016.
Examination Report for corresponding Australian Patent Application No. 2013290289 dated Mar. 27, 2017.
English language translation of Examination Report for corresponding Bolivian Patent Application No. SP 0207-2013 dated Nov. 10, 2014.
English language translation of Examination Report for corresponding Bolivian Patent Application No. SP 0207-2013 dated Feb. 15, 2016.
English language translation of Examination Report for corresponding Chilean Patent Application Chile Nr. 0051-2015 dated Jan. 27, 2016.
English language translation of Examination Report for corresponding Eurasian Patent Application 201590161 dated Jan. 27, 2016.
English language translation of Examination Report for corresponding Japanese Patent Application 2015-521752 dated Apr. 4, 2017.
Gokarn Y R et al., "Excipients for protein drugs", Excipient Development for Pharmaceutical, Biotechnology, and Drug Delivery Systems, p. 291-331; Jan. 1, 2006 (XP009179656).
Zimmer A, "Galenische Formulierung rekombinanter Wirkstoffe: Problem Arneistoffstabilitat", Pharmazie in Unserer Zeit, vol. 32, No. 5, p. 384-389; Sep. 1, 2003 (XP055109543).
Supplementary European Search Report for corresponding EP Application No. EP 12 84 2312.

ETANERCEPT FORMULATIONS STABILIZED WITH XYLITOL

CROSS REFERENCE TO RELATED APPLICATION

This application is a continuation U.S. Ser. No. 15/716,005 filed Sep. 26, 2017, which is a continuation of Ser. No. 15/209,484 filed Jul. 13, 2016, now U.S. Pat. No. 9,770,510, which is a divisional of U.S. Ser. No. 13/654,919 filed Oct. 18, 2012, now U.S. Pat. No. 9,393,305, which claims the benefit of U.S. Provisional Application Nos. 61/669,480 filed Jul. 9, 2012 and 61/548,518 filed Oct. 18, 2011, the disclosures of which are incorporated herein in their entirety by reference.

FIELD OF THE INVENTION

The present invention relates to aqueous pharmaceutical compositions stabilized with xylitol for long-term storage of etanercept, methods of manufacture of the compositions, methods of their administration, and kits containing the same. The invention includes etanercept formulations that do not require arginine for stabilization.

BACKGROUND OF THE INVENTION

Polypeptides must often be stored prior to their use. When stored for extended periods, polypeptides are frequently unstable in solution (Manning et al., 1989, Pharm. Res. 6:903-918). To extend their shelf life, additional processing steps have been developed, such as drying, e.g., lyophilization. However, lyophilized pharmaceutical compositions are less convenient to use.

Typical practices to improve polypeptide stability can be addressed by varying the concentration of elements with the formulation, or by adding excipients to modify the formulation (See, for example, U.S. Pat. Nos. 5,580,856 and 6,171,586). However, the use of additives can still result in inactive polypeptides. In addition, in the case of lyophilization, the rehydration step can result in inactivation of the polypeptide by, for example, aggregation or denaturation (Nora et al., 1992, Pharm. Res., 9:33-36; Liu et al., 1991, Biotechnol. Bioeng., 37:177-184). Aggregation of polypeptides is undesirable, as it may result in immunogenicity (Cleland et al., 1993, Crit. Rev. Therapeutic Drug Carrier Systems, 10:307-377; and Robbins et al., 1987, Diabetes, 36:838-845).

Another way to improve polypeptide stability is to use L-arginine at a specific concentration (U.S. Pat. No. 7,648,702).

One of the polypeptides that is stored for up to two years prior to use is etanercept (ENBREL® (etanercept), Immunex Corporation), which is a dimeric fusion polypeptide consisting of the extracellular ligand-binding portion of the human 75 kilodalton (p75) tumor necrosis factor receptor (TNFR) linked to the Fc portion of human IgG1. It consists of 934 amino acids and has an apparent molecular weight of approximately 150 kilodaltons (Physicians Desk Reference, 2002, Medical Economics Company Inc.) The Fc component of etanercept contains the constant heavy 2 (CH2) domain, the constant heavy 3 (CH3) domain and hinge region, but not the constant heavy 1 (CH1) domain of human IgG1. An Fc domain can contain one or all of the domains described above. Etanercept is usually produced by recombinant DNA technology in a Chinese hamster ovary (CHO) mammalian cell expression system.

The present invention provides novel stable liquid formulations of etanercept that allow its long-term storage.

SUMMARY OF THE INVENTION

The present invention is a stabilized aqueous pharmaceutical composition comprising etanercept and a stabilizer to inhibit instability, misfolding aggregation and/or fragmentation of the etanercept, wherein the stabilizer comprises xylitol or a combination of xylitol and meglumine.

Various technical terms used in the following discussion are defined below in the section entitled "Definitions" and throughout the remainder of the specification.

The stabilized etanercept formulations of the present invention which are optionally and preferably free of arginine, elicit long term storage stability as characterized by at least one of (1) SEC analysis at $M_3$ or $T_2$ or $T_4$ of: monomer content greater than about 90%; aggregates content of less than about 3 wt %; and fragment 3 content less than about 5 wt %: and (2) HIC analysis at $M_3$ or $T_2$, or $T_4$ wherein the amount of the composition represented by peak 1 of the HIC chromatogram is less than about 3 wt. %; the amount of the composition represented by peak 2 of the HIC chromatogram is greater than 80 wt. %; and the amount of the composition represented by peak 3 of the HIC chromatogram is less than about 20 wt %.

In preferred aspects of the stabilized formulations, the formulations elicit long term storage stability as characterized by: an HIC analysis at $M_3$ or $T_2$ or $T_4$ wherein the amount of the composition represented by peak 2 of the HIC chromatogram is greater than or equal to about 95 wt. %; and wherein, if peak 3 is present on the HIC chromatogram, the amount of the composition represented by peak 3 is less than or equal to about 3 wt. %.

The stabilized etanercept formulation as summarized above, optionally and preferably, contains no arginine, or are essentially free of arginine.

The formulations of the invention have excellent stability as determined by SEC (Size Exclusion Chromatography) and HIC (Hydrophobic Interaction Chromatography) analysis conducted after one, two or three months of storage at 5° C. These formulations are comparable to or better than a commercially available formulation of etanercept, in which arginine is a required component. Accordingly the present invention is further directed to formulations of stabilized etanercept, as summarized above, which contain no arginine, or are essentially free of arginine, and wherein the composition, evaluated at $M_3$ or $T_2$ or $T_4$, elicits long term storage stability that meets one or both of the following criteria: (A) stability comparable to or better than commercially available etanercept marketed under the trademark ENBREL® (etanercept), as measured by (i) SEC analysis of the amounts of aggregate(s), monomer and fragment 3 in the composition (as defined in the specification) and (ii) HIC analysis of amounts of material in the composition corresponding to peaks 1, 2 and 3 of the HIC chromatogram (as defined in the specification); and (B) an HIC chromatogram in which (i) peak 3 is absent, or essentially absent and (ii) peak 2 represents greater than about 95 wt % of the composition; an SEC chromatogram containing essentially no peak corresponding to aggregate(s); and an SEC chromatogram in which the monomer content represents at least about 95 wt % of the composition.

In one preferred aspect, the formulation of the invention comprises about about 25 to about 75 mg/ml of etanercept; and a stabilizer to inhibit instability, aggregation and/or fragmentation of the etanercept, wherein the stabilizer is xylitol in an amount constituting up to about 10 wt. % of the composition, and wherein the composition is characterized by an SEC analysis at $M_3$ or $T_2$ or $T_4$ of greater than about 80 wt. % monomer content; less than about 3 wt % aggregate(s) content; and less than about 6 wt % fragment 3 content and having a pH of 6.0 to 6.6. Formulations meeting these analytical criteria do not require arginine for stabilization.

In a further preferred embodiment the stabilized etanercept formulation is further characterized by (a) an SEC analysis at $M_3$ or $T_2$ or $T_4$ of greater than about 90 wt % monomer content; and less than about 3 wt % aggregate(s) content; and (b) an HIC analysis at $M_3$ or $T_2$ or $T_4$ wherein the amount of the composition represented by peak 1 of the HIC chromatogram is less than about 4 wt %; the amount of the composition represented by peak 2 of the HIC chromatogram is greater than about 80 wt %; and the amount of the composition represented by peak 3 of the HIC chromatogram is less than about 20 wt %. Formulations meeting these analytical criteria do not require arginine for stabilization.

The etanercept compositions of the invention further afford the ability to provide formulations which contain acceptable levels of subvisible particles. Accordingly, the invention is further directed to stabilized etanercept formulations having, at $M_3$ or $T_2$ or $T_4$, no more than, on average, about 10,000 subvisible particles per mL having a size greater than 5 μm.

The stabilized etanercept composition of the present invention are further characterized by: (a) an SEC analysis at $M_3$ or $T_2$ or $T_4$ of greater than about 90 wt % monomer content; and less than about 3 wt % aggregate(s) content; and (b) an HIC analysis at $M_3$ or $T_2$ or $T_4$ wherein the amount of the composition represented by peak 1 of the HIC chromatogram is less than about 3 wt %; the amount of the composition represented by peak 2 of the HIC chromatogram is greater than 80 wt %; and the amount of the composition represented by peak 3 of the HIC chromatogram is less than about 20 wt % and wherein the formulation is free or essentially free of arginine.

The stability of the formulations may be further characterized in that the compositions, optionally free or essentially of arginine, exhibit an HIC analysis at $M_3$ or $T_2$ or $T_4$ wherein the amount of the composition represented by peak 1 of the HIC chromatogram is less than about 1%; the amount of the composition represented by peak 2 of the HIC chromatogram is greater than about 95 wt %; and the amount of the composition represented by peak 3 of the HIC chromatogram is less than about 3 wt %.

Preferred stabilized compositions of the invention, preferably free or essentially free of arginine, exhibit an HIC analysis at $M_3$ or $T_2$ or $T_4$ wherein the amount of the composition represented by peak 1 of the HIC chromatogram is less than about 2% or preferably less than about 1%; the amount of the composition represented by peak 2 of the HIC chromatogram is greater than about 95 wt. % and preferably greater than about 97%; and the amount of the composition represented by peak 3 of the HIC chromatogram is less than about 1 wt %, and preferably 0 to 1%. Formulations meeting these analytical criteria do not require arginine for stabilization.

The stabilized etanercept formulations may contain in addition to xylitol, the further optional ingredients meglumine, sucrose and sodium chloride. Thus, the invention is further directed to compositions comprising about 25 to 75 mg/ml of etanercept; about 1-10 wt % xylitol; about 1 to 30 mM sodium phosphate; optionally up to about 5 wt. % meglumine; optionally up to about 5 mM NaCl; and optionally up to about 5 wt. % sucrose.

As differentiated from commercially available etanercept provided in an arginine-containing formulation, we found it surprising, in light of U.S. Pat. No. 7,648,702, that the formulation embodiments of etanercept described and exemplified herein do not require arginine for long-term stabilization, although arginine may still be added if desired. The ability to provide etanercept formulations stabilized without arginine represents a potentially significant benefit to the health care system by providing patients and health care providers with alternative formulations of etanercept that may become available at lower cost compared with present commercial etanercept formulation (i.e., Enbrel®) that require arginine for stabilization.

As used herein the term "instability" or like terms denotes the tendency of the etanercept monomer to undergo a variety of undesired transformations during storage. Such transformations include the formation of oligomers and high molecular weight aggregate(s) (hereinafter terms "aggregate(s)" in which multiple copies of the essentially intact etanercept monomer become irreversibly associated with one another through a variety of non-covalent attractions (e.g., electrostatic interactions.) Undesired transformations during storage may also include degradation of the etanercept monomer to smaller fragments and/or dipped species. Ideally, a formulation of etanercept should minimize, to the greatest extent possible, the tendency of the formulation to result, during storage, in the formation of aggregates, misfolded protein, oligomers and/or fragments of etanercept. An important benefit resulting from the ability to reduce formation of unwanted aggregates or fragments is a reduction in the potential toxicity and/or immunogenicity of the drug.

The etanercept formulation of the present invention which is optionally and preferably free, or essentially free of arginine. The term "essentially free of arginine" is intended to mean that arginine, even if present, is not contributing to the stabilization of the etanercept monomer in the formulation to such an extent that a person skilled in the art would judge its presence beneficial or necessary from a stabilization standpoint.

These and other aspects will become apparent from the following description although variations and modifications therein may be affected without departing from the spirit and scope of the novel concepts of the disclosure.

It is to be understood that both the foregoing general description and the following detailed description are exemplary and explanatory only and are not restrictive of the invention, as claimed.

DETAILED DESCRIPTION OF THE INVENTION

Various embodiments of the invention are now described in detail. As used in the description and throughout the claims, the meaning of "a", "an", and "the" includes plural reference unless the context dearly dictates otherwise. Also, as used in the description and throughout the claims, the meaning of "in" includes "in" and "on" unless the context dearly dictates otherwise. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. The invention is not limited to the various embodiments given in this specification.

Unless otherwise defined, all technical and scientific terms used herein have the same meaning as commonly understood by one of ordinary skill in the art to which this invention pertains. In the case of conflict, the present document, including definitions will control.

"Around," "about" or "approximately" shall generally mean within 20 percent, within 10 percent, within 5, 4, 3, 2 or 1 percent of a given value or range. Numerical quantities given are approximate, meaning that the term "around," "about" or "approximately" can be inferred if not expressly stated.

The term "etanercept" or "etanercept monomer" or "monomer" is synonymous with Enbrel®. It refers to a polypeptide which is a dimeric fusion polypeptide consisting of the extracellular ligand-binding portion of the human 75 kilodalton (p75) tumor necrosis factor receptor (TNFR) linked to the Fc portion of human IgG1. It consists of 934 amino acids and has an apparent molecular weight of approximately 150 kilodaltons. For the purposes of the present application, the term "etanercept" also encompasses etanercept with minor modifications in the amino acid structure (including deletions, additions, and/or substitutions of amino adds) which do not significantly affect the function, potency, or avidity of etanercept. The term "etanercept" encompasses all forms and formulations of Enbrel®, including but not limited to concentrated formulations, injectable ready-to-use formulations; formulations reconstituted with water, alcohol, and/or other ingredients, and others.

The term "sugar" refers to monosaccharides, disaccharides, and polysaccharides. Examples of sugars include, but are not limited to, sucrose, trehalose, dextrose, and others.

The term "meglumine" refers to a compound with chemical formula $H_3NHCH_2(CHOH)_4CH_2OH$, also known as 1-Deoxy-1-methylaminosorbitol; N-Methyl-d-glucamine; and 1-Deoxy-1-methylamino-D-glucitol.

The terms "mannosylglycerate," "mannosyllactate," "mannosylglycolate, and "diglycerolphosphate" are well known in the art and have their commonly accepted meanings. The following references describe these compounds in some detail: Faria et al., *Carbohydrate Res.* 2008, 343: 3025-3033; Borges et al., *Extremophiles* 2002, 6: 209-216; Faria et al., *ChemBioChem* 2003, 4: 734-741; Sawangwan et al., *Biotechnol. J.* 2010, 5: 187-191; and Pals et al., *J. Mol. Biol.* 2009, 394: 237-250. The application incorporates by reference the description of these compounds contained in these references.

The term polyol" refers to an alcohol containing multiple hydroxyl groups. Examples of polyols include, but are not limited to, mannitol, sorbitol, and others.

The term "long-term storage" is understood to mean that the pharmaceutical composition can be stored for three months or more, for six months or more, and preferably for one year or more. Long term storage is also understood to mean that the pharmaceutical composition is stored either as a liquid at 2-8° C., or is frozen, e.g., at −20° C., or colder. It is also contemplated that the composition can be frozen and thawed more than once.

The term "stable" or "stabilized" with respect to long-term storage is understood to mean that etanercept contained in the pharmaceutical compositions does not lose more than 20%, or more preferably 15%, or even more preferably 10%, and most preferably 5% of its activity relative to activity of the composition at the beginning of storage.

The term "mammal" includes, but is not limited to, a human.

The term "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed and is compatible with other ingredients of the formulation.

The term "composition" refers to a mixture that usually contains a carrier, such as a pharmaceutically acceptable carrier or excipient that is conventional in the art and which is suitable for administration into a subject for therapeutic, diagnostic, or prophylactic purposes. It may include a cell culture in which the polypeptide or polynucleotide is present in the cells or in the culture medium. For example, compositions for oral administration can form solutions, suspensions, tablets, pills, capsules, sustained release formulations, oral rinses or powders.

The terms "pharmaceutical composition" and "formulation" are used interchangeably.

The term "treatment" refers to any administration or application of remedies for disease in a mammal and includes inhibiting the disease, arresting its development, relieving the disease, for example, by causing regression, or restoring or repairing a lost, missing, or defective function; or stimulating an inefficient process. The term includes obtaining a desired pharmacologic and/or physiologic effect, covering any treatment of a pathological condition or disorder in a mammal. The effect may be prophylactic in terms of completely or partially preventing a disorder or symptom thereof and/or may be therapeutic in terms of a partial or complete cure for a disorder and/or adverse affect attributable to the disorder. It includes (1) preventing the disorder from occurring or recurring in a subject who may be predisposed to the disorder but is not yet symptomatic, (2) inhibiting the disorder, such as arresting its development, (3) stopping or terminating the disorder or at least its associated symptoms, so that the host no longer suffers from the disorder or its symptoms, such as causing regression of the disorder or its symptoms, for example, by restoring or repairing a lost, missing or defective function, or stimulating an inefficient process, or (4) relieving, alleviating or ameliorating the disorder, or symptoms associated therewith, where ameliorating is used in a broad sense to refer to at least a reduction in the magnitude of a parameter, such as inflammation, pain and/or tumor size.

The term "disease" refers to any condition, infection, disorder or syndrome that requires medical intervention or for which medical intervention is desirable. Such medical intervention can include treatment, diagnosis and/or prevention.

The term "therapeutically effective amount" refers to an amount which, when administered to a living subject, achieves a desired effect on the living subject. For example, an effective amount of the polypeptide of the invention for administration to the living subject is an amount that prevents and/or treats an integrin αvβ3-mediated disease. The exact amount will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art.

The term "$T_1$" refers to a point in time at which an etanercept formulation has been stored for about one week at 40° C.

The term "$T_2$" refers to a point in time at which an etanercept formulation has been stored for about two weeks at 40° C.

The term "$T_4$" refers to a point in time at which an etanercept formulation has been stored for about four weeks at 40° C.

The term "$M_3$" refers, collectively, to three points in time, and in particular to an analytical result being observed for an etanercept formulation after duration of either about one, about two or about three months of storage at a storage temperature of 5° C. For example, reference herein to an analysis being conducted at $M_3$ should be understand to mean that such analysis is be done at the point in time at which etanercept formulation has been in storage for a duration selected from about one, about two, or about three months. Thus, a requirement herein that an etanercept formulation elicit a certain analytical value or measurement at $M_3$ is satisfied if the required value is observed at a point in time corresponding to at least one of the following storage durations: at approximately one month, at approximately two months or at approximately three months of storage at 5° C.

The terms "Peak 1," "Peak 2" and "Peak 3" when used herein in connection with discussion of HIC chromatography results refers to the same peaks 1, 2 and 3 discussed in U.S. Pat. No. 7,294,481.

EMBODIMENTS OF THE INVENTION

When pharmaceutical compositions containing etanercept (ENBREL® (etanercept)), including aqueous and lyophilized formulations of etanercept are stored on a long term basis, the activity of etanercept can be lost or decreased due to instability of the etanercept monomer via aggregation and/or chemical degradation including formation of fragments and oligomers. Thus, the present invention provides several embodiments of aqueous formulations of etanercept that allow stable long-term storage of etanercept, so that etanercept is stable over the course of storage either in liquid or frozen states. The provided formulations include, but are not limited to formulations that do not contain arginine and do not require any extra steps such as rehydrating.

These embodiments are explained in a greater detail below.

Etanercept

All of the compositions of the present invention comprise etanercept (ENBREL®). As explained in the Background section of this application, etanercept is a dimeric fusion polypeptide consisting of the extracellular ligand-binding portion of the human 75 kilodalton (p75) tumor necrosis factor receptor (TNFR) linked to the Fc portion of human IgG1. Etanercept consists of 934 amino adds. The Fc component of etanercept contains the constant heavy 2 (CH2) domain, the constant heavy 3 (CH3) domain and hinge region of human IgG1. An Fc domain can contain one or all of the domains described above.

Etanercept suitable for storage in the present pharmaceutical composition can be produced by living host cells that express etanercept, such as hybridomas in the case of antibodies, or host cells that that have been genetically engineered to produce the polypeptide in the case of fusion polypeptides or antibodies. Methods of genetically engineering cells to produce polypeptides are well known in the art. See, e.g., Ausubel et al., eds. (1990), Current Protocols in Molecular Biology (Wiley, New York). Such methods include introducing nucleic adds that encode and allow expression of the polypeptide into living host cells. These host cells can be bacterial cells, fungal cells, or, preferably, animal cells grown in culture. Bacterial host cells include, but are not limited to, *Escherichia coli* cells. Examples of suitable *E. coli* strains include: HB101, DH5.alpha, GM2929, JM109, KW251, NM538, NM539, and any *E. coli* strain that fails to cleave foreign DNA. Fungal host cells that can be used include, but are not limited to, *Saccharomyces cerevisiae, Pichia pastoris* and *Aspergillus* cells. A few examples of animal cell lines that can be used are CHO, VERO, BHK, HeLa, Cos, MDCK, 293, 3T3, and W138. New animal cell lines can be established using methods well know by those skilled in the art (e.g., by transformation, viral infection, and/or selection). Optionally, etanercept can be secreted by the host cells into the medium.

Purification of the expressed etanercept can be performed by any standard method. When etanercept is produced intracellularty, the particulate debris is removed, for example, by centrifugation or ultrafiltration. When etanercept is secreted into the medium, supernatants from such expression systems can be first concentrated using standard polypeptide concentration filters. Protease inhibitors can also be added to inhibit proteolysis and antibiotics can be included to prevent the growth of microorganisms.

Etanercept can be purified using, for example, hydroxyapatite chromatography, gel electrophoresis, dialysis, and affinity chromatography, and any combination of known or yet to be discovered purification techniques, including but not limited to Protein A chromatography, fractionation on an ion-exchange column, ethanol precipitation, reverse phase HPLC, chromatography on silica, chromatography on heparin SEPHAROSET®, an anion or cation exchange resin chromatography (such as a polyaspartic add column), chromatofocusing, SDS-PAGE, and ammonium sulfate precipitation.

Etanercept Stabilized with Xylitol

The invention provides a stabilized aqueous pharmaceutical composition comprising etanercept and a stabilizer to inhibit instability, aggregation and/or fragmentation of the etanercept, wherein the stabilizer comprises xylitol or a combination of xylitol and meglumine.

Without wishing to be bound to any particular theory, it is believed that xylitol reduces etanercept's tendency to associate in undesired ternary or quaternary complexes, and therefore, reduces aggregation of etanercept. Presumably, xylitol acts as a conformational stabilizer, thereby reducing the propensity of etanercept to aggregate. The reduction in aggregation is believed to last for a long period of time, e.g., two years or more. The stabilizing effects of xylitol are not limited to reduction in aggregates but may involve other aspects of stabilization of etanercept.

A preferred stabilized etanercept formulation incorporating xylitol for stabilization is one in which stabilization is provided by a combination of xylitol and meglumine.

The pharmaceutical compositions of the invention may be prepared by combining, a purified etanercept and xylitol, or xylitol in combination with meglumine. Further, a buffer, a tonicity modifier and an additional excipient and other commonly used inactive ingredients can be added as needed. For simplicity, these are discussed more fully later in the specification. A person of ordinary skill in the art will understand that the combining of the various components to be included in the composition can be done in any appropriate order. For example, the buffer can be added first, middle or last, and the tonicity modifier can also be added first, middle or last. A person of ordinary skill in the art will also understand that some of these chemicals can be incompatible in certain combinations, and accordingly, are easily substituted with different chemicals that have similar properties but are compatible in the relevant mixture.

Xylitol stabilized etanercept formulations of the invention can comprise about 25 to 75 mg/ml of etanercept; about 1-10 wt. % xylitol; about 1 to 30 mM sodium phosphate; optionally up to about 5 wt. % meglumine; optionally up to about 5 mM NaCl; and optionally up to about 5 wt. % sucrose.

Xylitol stabilized etanercept formulations which additionally contain meglumine, sodium chloride and sucrose can comprise, in addition to xylitol, comprise about 1-100 mM NaCl; about 1 to 5 wt. % sucrose; and meglumine in an amount of about 1-5 wt % of the composition.

In place of meglumine, the present invention also contemplates the use of mannosylglycerate, "mannosyllactate, mannosylglycolate, and diglycerolphosphate.

In a further embodiment, xylitol stabilized etanercept formulations can comprise about 25 to about 75 mg/ml of etanercept; and a stabilizer to inhibit instability, aggregation and/or fragmentation of the etanercept, wherein the stabilizer is xylitol in an amount constituting up to about 10 wt. % of the composition, and wherein the composition is characterized by an SEC analysis at $T_2$ of: about 80 wt. % to about 95 wt % monomer content; an SEC analysis at $T_2$ of aggregate(s) content of less than about 4 wt. % and preferably less than about 3 wt %; and an SEC analysis at $T_2$ of fragment 3 content of less than about 8 wt. % and preferably less than about 6 wt. %; wherein the composition has a pH of about 6.0 to about pH 7.0, and more preferably about 6.0 to about 6.6 and most preferably about 6.3 to about 6.5.

In stabilized etanercept formulations such as those referenced above containing xylitol or xylitol in combination with meglumine, the formulations are more preferably characterized by:
 (a) an SEC analysis at $T_4$ of greater than about 90, 91, 92, 93, 94, 95, 96, or 97 wt. % monomer content; and less than about 3, 2 or 1 wt % aggregate(s) content; and
 (b) an HIC analysis at $T_2$ wherein the amount of the composition represented by peak 1 of the HIC chromatogram is less than about 3, 2 or 1 wt. %; the amount of the composition represented by peak 2 of the HIC chromatogram is greater than 80, 81, 82, 83, 84 or 85 wt. %; and the amount of the composition represented by peak 3 of the HIC chromatogram is less than about 20, 19, 18, 17, 16, 15, 14, or 13 wt %; and
 (c) an HIC analysis at $T_4$ wherein the amount of the composition represented by peak 1 of the HIC chromatogram is less than about 3, 2 or 1 wt %; the amount of the composition represented by peak 2 of the HIC chromatogram is greater than 80, 81, 82, 83, 84 or 85 wt. %; and the amount of the composition represented by peak 3 of the HIC chromatogram is less than 20, 19, 18, 17, 16, 15, 14 or 13 wt. %.

The terms "SEC", "$T_2$," "$T_4$," "HIC" "monomer content" "aggregate(s)" and "fragment 3" "peak 1," "peak 2," and "peak 3," are defined in the examples below.

Particularly preferred formulations containing xylitol, or xylitol in combination with meglumine are characterized by having an HIC analysis at $T_4$ or $T_2$ wherein the amount of the composition represented by peak 1 of the HIC chromatogram is less than about 1%; the amount of the composition represented by peak 2 of the HIC chromatogram is greater than about 95 wt. % and preferably greater than about 99 wt. %; and the amount of the composition represented by peak 3 of the HIC chromatogram is less than about 1 wt. %. Specific xylitol-stabilized formulations are provided in the detailed examples.

Although the invention does not exclude the use of arginine, the etanercept formulations comprising xylitol for stabilization according to the present invention are free or essentially free of arginine.

Additional Components of the Provided Pharmaceutical Compositions

The formulations of the invention may also include buffers, tonicity modifiers, excipients, pharmaceutically acceptable carriers and other commonly used inactive ingredients of the pharmaceutical compositions. For simplicity, these are discussed more fully later in the application.

Buffers maintain pH in a desired range. Suitable buffers include histidine, potassium phosphate, sodium or potassium citrate, maleic acid, ammonium acetate, tris-(hydroxymethyl)-aminomethane (tris), various forms of acetate and diethanolamine. The concentration of the buffer in the formulation is preferably between about 1 mM to about 1M, and more preferably about 10 mM to about 200 mM. Buffers are well known in the art and are manufactured by known methods and available from commercial suppliers.

Examples of suitable buffers are phosphate, histidine, citrate, maleate, tartrate, succinate, acetate, tris-(hydroxymethyl)-aminomethane (tris), bicarbonate.

In a preferred embodiment, the buffer is sodium phosphate.

In a preferred embodiment, the pH of the pharmaceutical composition is at or near physiological levels. Thus, preferably, the pH of the provided compositions is between about 5.8 and about 8.4; and even more preferably, between about 6.2 and about 7.4. A person of ordinary skill in the art will understand that the pH can be adjusted as necessary to maximize stability and solubility of etanercept in a particular formulation. Thus, etanercept formulations at a pH outside of physiological ranges, yet tolerable to the patient, are also within the scope of the invention.

A tonicity modifier is a molecule that contributes to the osmolality of a solution. The osmolality of a pharmaceutical composition is preferably adjusted to maximize the active ingredient's stability and/or to minimize discomfort to the patient upon administration. It is generally preferred that a pharmaceutical composition be isotonic with serum, i.e., having the same or similar osmolality, which is achieved by addition of a tonicity modifier.

In a preferred embodiment, the osmolality of the provided formulations is from about 180 to about 420 mOsM. However, it is to be understood that the osmolality can be either higher or lower as specific conditions require.

Examples of tonicity modifiers suitable for modifying osmolality include, but are not limited to amino acids (not including arginine) (e.g., cysteine, histidine and glycine), salts (e.g., sodium chloride, potassium chloride and sodium citrate) and/or saccharides (e.g., sucrose, glucose and mannitol).

Preferred tonicity modifiers are glycine, alanine, sodium chloride, potassium chloride, and sodium sulfate.

In a preferred embodiment, the concentration of the tonicity modifier in the formulation is preferably between about 1 mM to about 1 M, more preferably about 10 mM to about 200 mM. Tonicity modifiers are well known in the art and are manufactured by known methods and available from commercial suppliers.

Excipients, also referred to as chemical additives, co-solutes, or co-solvents, that stabilize the polypeptide while in solution (also in dried or frozen forms) can also be added to a pharmaceutical composition. Excipients are well known in the art and are manufactured by known methods and available from commercial suppliers.

Examples of suitable excipients include but are not limited to sugars/polyols such as: sucrose, lactose, glycerol, xylitol, sorbitol, mannitol, maltose, inositol, trehalose, glucose; polymers such as: serum albumin (bovine serum albumin (BSA), human SA or recombinant HA), dextran, poly(viny alcohol) PVA, hydroxypropyl methylcellulose (HPMC), polyethyleneimine, gelatin, polyvinylpyrrolidone (PVP), hydroxyethylcellulose (HEC); non-aqueous solvents such as: polyhydric alcohols, (e.g., PEG, and glycerol) and dimethylformamide (DMF); amino acids such as: proline, L-serine, sodium glutamic acid, alanine, glycine, lysine hydrochloride, sarcosine and gamma-aminobutyric add; surfactants such as: Tween®-80 (polysorbate 80), Tween®-20 (polysorbate 20), SDS, polysorbate, poloxamers; and miscellaneous excipients such as: potassium phosphate, sodium acetate, ammonium sulfate, magnesium sulfate, sodium sulfate, trimethylamine N-oxide, betaine, metal ions (e.g., zinc, calcium, and magnesium), CHAPS, monolaurate, 2-O-beta-mannoglycerate or any combination of the above.

Preferred excipients are sucrose, lactose, glycerol, xylitol, sorbitol, mannitol, maltose, inositol, trehalose, glucose, bovine serum albumin (BSA), human serum albumin (HSA), recombinant albumin, dextran, PVA, hydroxypropyl methylcellulose (HPMC), polyethyleneimine, gelatin, polyvinylpyrrolidone (PVP), hydroxyethylcellulose (HEC), polyethylene glycol, ethylene glycol, glycerol, alanine, glycine, lysine hydrochloride, sarcosine, SDS, polysorbate 20, polysorbate 80, poloxamer 188, trimethylamine N-oxide, betaine, zinc ions, calcium ions, magnesium ions, CHAPS, sucrose monolaurate, and 2-O-beta-mannoglycerate.

The concentration of one or more excipients in a formulation of the invention is/are preferably between about 0.001 to 5 weight percent, more preferably about 0.1 to 2 weight percent.

Methods of Treatment

In another embodiment, the invention provides a method of treating a mammal comprising administering a therapeutically effective amount of the pharmaceutical compositions of the invention to a mammal, wherein the mammal has a disease or disorder that can be beneficially treated with etanercept.

In a preferred embodiment, the etanercept is derived from the same species of mammal as is to be treated with the composition.

In a preferred embodiment, the mammal is a human.

Diseases or disorders that can be treated with the provided compositions include but are not limited to rheumatoid arthritis, psoriatic arthritis, ankylosing spondylitis, Wegener's disease (granulomatosis), Crohn's disease (or inflammatory bowel disease), chronic obstructive pulmonary disease (COPD), Hepatitis C, endometriosis, asthma, cachexia, psoriasis, and atopic dermatitis. Additional diseases or disorders that can be treated with the compositions of the present invention include those described in WO 00/62790, WO 01/62272, U.S. Patent Application No. 2001/0021380, and U.S. Pat. No. 7,648,702 B2, the relevant portions of which are incorporated herein by reference.

The provided pharmaceutical compositions may be administered to a subject in need of treatment by injection systemically, such as by intravenous injection; or by injection or application to the relevant site, such as by direct injection, or direct application to the site when the site is exposed in surgery; or by topical application.

In one embodiment, the invention provides a method of treatment and/or prevention of rheumatoid arthritis comprises administering to a mammal in need thereof a therapeutically effective amount of one of the provided etanercept compositions.

The therapeutically effective amount of the etanercept in the provided compositions will depend on the condition to be treated, the severity of the condition, prior therapy, and the patient's clinical history and response to the therapeutic agent. The proper dose can be adjusted according to the judgment of the attending physician such that it can be administered to the patient one time or over a series of administrations.

In one embodiment, the effective etanercept amount per adult dose is from about 1-500 mg/m$^2$, or from about 1-200 mg/m$^2$, or from about 1-40 mg/m$^2$ or about 5-25 mg/m$^2$.

Alternatively, a flat dose may be administered, whose amount may range from 2-500 mg/dose, 2-100 mg/dose or from about 10-80 mg/dose.

If the dose is to be administered more than one time per week, an exemplary dose range is the same as the foregoing described dose ranges or lower and preferably administered two or more times per week at a per dose range of 25-100 mg/dose.

In another embodiment, an acceptable dose for administration by injection contains 80-100 mg/dose, or alternatively, containing 80 mg per dose.

The dose can be administered weekly, biweekly, or separated by several weeks (for example 2 to 8).

In one embodiment, etanercept is administered at 25 to 75 mg/ml by a single subcutaneous (SC) injection.

In some instances, an improvement in a patient's condition will be obtained by administering a dose of up to about 100 mg of the pharmaceutical composition one to three times per week over a period of at least three weeks. Treatment for longer periods may be necessary to induce the desired degree of improvement. For incurable chronic conditions the regimen may be continued indefinitely. For pediatric patients (ages 4-17), a suitable regimen may involve administering a dose of 0.4 mg/kg to 5 mg/kg of etanercept, one or more times per week.

In another embodiment, the pharmaceutical formulations of the invention may be prepared in a bulk formulation, and as such, the components of the pharmaceutical composition are adjusted to be higher than would be required for administration and diluted appropriately prior to administration.

The pharmaceutical compositions can be administered as a sole therapeutic or in combination with additional therapies as needed. Thus, in one embodiment, the provided methods of treatment and/or prevention are used in combination with administering a therapeutically effective amount of another active agent. The other active agent may be administered before, during, or after administering the pharmaceutical compositions of the present invention. Another active agent may be administered either as a part of the provided compositions, or alternatively, as a separate formulation.

Administration of the provided pharmaceutical compositions can be achieved in various ways, including parenteral, peroral, buccal, sublingual, nasal, rectal, intraperitoneal, intradermal, transdermal, subcutaneous, intravenous, intra-arterial, intracardiac, intraventricular, intracranial, intratracheal, intrathecal administration, intramuscular injection, intravitreal injection, and topical application.

The pharmaceutical compositions of this invention are particularly useful for parenteral administration, i.e., subcutaneously, intramuscularly, intravenously, intraperitoneal, intracerebrospinal, intra-articular, intrasynovial, intravitreal, and/or intrathecal. Parenteral administration can be by bolus injection or continuous infusion. Pharmaceutical compositions for injection may be presented in unit dosage form, e.g., in ampoules or in multi-dose containers, with an added preservative. In addition, a number of recent drug delivery approaches have been developed and the pharmaceutical compositions of the present invention are suitable for administration using these new methods, e.g., Inject-ease®, Genject, injector pens such as GenPen®, and needleless devices such as MediJector® and BioJector®. The present pharmaceutical composition can also be adapted for yet to be discovered administration methods. See also Langer, 1990, Science, 249:1527-1533.

The provided pharmaceutical compositions can also be formulated as a depot preparation. Such long acting formulations may be administered by implantation (for example subcutaneously or intramuscularly) or by intramuscular injection. Thus, for example, the formulations may be modified with suitable polymeric or hydrophobic materials (for example as an emulsion in an acceptable oil) or ion exchange resins, or as sparingly soluble derivatives, for example, as a sparingly soluble salt.

The pharmaceutical compositions may, if desired, be presented in a vial, pack or dispenser device which may contain one or more unit dosage forms containing the active ingredient. In one embodiment the dispenser device can comprise a syringe having a single dose of the liquid formulation ready for injection. The syringe can be accompanied by instructions for administration.

In another embodiment, the present invention is directed to a kit or container, which contains an aqueous pharmaceutical composition of the invention. The concentration of the polypeptide in the aqueous pharmaceutical composition can vary over a wide range, but is generally within the range of from about 0.05 to about 20,000 micrograms per milliliter (μg/ml) of aqueous formulation. The kit can also be accompanied by instructions for use.

The present invention is more particularly described in the following examples that are intended as illustrative only, since many modifications and variations therein will be apparent to those skilled in the art.

Example

Etanercept Stabilized with Xylitol

Etanercept formulations stabilized with xylitol, preferably without arginine, may be prepared and tested using the procedures generally described below.

Each solid formulation component is weighed to the amount required for a given volume of formulation buffer. These components are combined into a beaker or vessel capable of carrying and measuring the given volume of formulation buffer. A volume of deionized water equal to approximately ¾ of the target given formulation buffer is added to the beaker, and the components are then solubilized. The pH of the buffer is adjusted to the target formulation pH using 1 M sodium hydroxide and/or 1 M hydrogen chloride. The final formulation buffer volume is then raised to the target volume through the addition of deionized water. Etanercept protein solution is placed in dialysis material housing (such as Thermo Scientific Slide-A-Lyzer MINI Dialysis Unit 10,000 MWCO), which is then placed in contact with the desired formulation buffer for 12 hours at 4° C. Formulation buffer volume to protein solution volume ratio should be no less than 1000:1. The dialysis housing and protein solution it contains is then placed in a second, equal volume of formulation buffer for an additional 12 hours at 4° C. Resulting protein solution is removed from the dialysis material housing, and the concentration of protein determined using ultraviolet spectroscopy. Protein concentration is adjusted to the desired level using centrifugation (such as Amicon Ultra 10,000 MWCO Centrifugal Concentrators) and/or dilution with formulation buffer.

The compositions can be tested for long-term stability by size exclusion chromatography (SEC), denatured SEC (dSEC), hydrophobic interaction chromatography (HIC), sodium dodecylsulfate polyacrylamide gel electrophoresis (SDS-PAGE), and for binding and bioactivity at various timepoints. The bioactivity can be measured by any number of well-known assays.

For example, the techniques of Size Exclusion Chromatography are described in Hawe at al, Pharm. Res. 2011, 28: 2302 and/or van Marrschalkerweerd et al., Eur. J. Pharm. Biopharm. 2011, 78: 213. Similarly, the techniques of Denatured Size Exclusion Chromatography, Hydrophobic Interaction Chromatography, and Sodium DodecylSulfate-PolyAcrylamide Gel Electrophoresis are also well known to persons having ordinary skill in the art.

It is believed that the composition will be stable over the term of two years or more. The compositions exemplified below do not contain arginine.

Formulation 1:17

| Ingredient | concentration |
| --- | --- |
| Etanercept (active ingredient) | 50 mg/ml |
| Sodium phosphate, pH 6.3 (inactive) | 25 mM |
| Xylitol (inactive) | 10% (w/v) |

Formulation 2:10

| Ingredient | concentration |
| --- | --- |
| Etanercept (active ingredient) | 50 mg/ml |
| Sodium phosphate, pH 6.31 (inactive) | 25 mM |
| Xylitol (inactive) | 6% (w/v) |

Formulation 2:11

| Ingredient | concentration |
| --- | --- |
| Etanercept (active ingredient) | 50 mg/ml |
| Sodium phosphate, pH 6.3 (inactive) | 25 mM |
| Xylitol (inactive) | 2.5% (w/v) |
| Sucrose (inactive ingredient) | 5% (w/v) |

Formulation 2:18

| Ingredient | concentration |
| --- | --- |
| Etanercept (active ingredient) | 50 mg/ml |
| Sodium phosphate, pH 6.4 (inactive) | 25 mM |
| Xylitol (inactive) | 2.5% (w/v) |
| Meglumine (inactive) | 2.5% (w/v) |

Formulation 2:19

| Ingredient | concentration |
| --- | --- |
| Etanercept (active ingredient) | 50 mg/ml |
| Sodium phosphate, pH 6.24 (inactive) | 10 mM |
| Xylitol (inactive) | 2.5% (w/v) |
| Meglumine (inactive) | 2.5% (w/v) |
| NaCl (inactive) | 2.5% (w/v) |
| Sucrose (inactive) | 1% (w/v) |

Example 2

Preparation of Etanercept

Step 1. Cell Expansion.

In a manner known in the art, cell expansion necessary to generate a sufficient number of cells for inoculation of a production bioreactor is performed using a clone of CHO cells expressing the etanercept fusion protein. The product of this expression process (a harvested cell culture fluid) results in a mixture of correctly folded etanercept, as well as incorrectly folded and/or aggregated etanercept, along with additional impurities. The harvested cell culture fluid comprising such protein mixture is subjected to detergent viral inactivation.

Step 2.

Affinity Chromatography. Affinity chromatography is performed on the harvested cell culture obtain in Step 1 above using a conventional Protein A affinity column in a well known manner. Product recovery is approximately 85%. The product obtained is a complex protein mixture comprising correctly folded etanercept, incorrectly folded etanercept, and/or aggregates of correctly and/or incorrectly folded etanercept, or protein fragments. The product obtained from this Protein A affinity column purification step is adjusted to pH 3.5 and then subjected to a viral inactivation step. Following viral inactivation the product is adjusted to pH 5.5 and then further clarified in a known manner using a commercially obtained capsule filter.

Step 3A.

Mixed-Mode Cation Exchange Chromatography. A 31.8 L (45 cm diameter×20 cm bed height) packed bed GE Healthcare Capto MMC chromatography column is used to purify the product obtained in Step 2 above. Prior to use, the column is equilibrated with 2 CV of 25 mM acetate pH 5.5 and sanitized with 2 CV of 0.1 N NaOH, 1 M NaCl and neutralized with 2 CV of 25 mM acetate, 0.7 M NaCl, pH 5.5. The column is then equilibrated with 8-10 CV of 25 mM acetate pH 5.5 until the effluent is pH 5.5 and 3.5 mS/cm. The Protein A pool from step 2 above is diluted to ≤6 mS/cm with WFI and applied to a column loading of up to 15 g/L media for each cycle. The column is operated at a linear velocity of 200 cm/h to give a 6 minute residence time. After loading, the column is washed with 2 CV of 25 mM acetate pH 5.5. The product is then eluted with an 8.5 CV, 15% to 85% gradient of 25 mM acetate pH 5.5 to 25 mM acetate, 0.7 M NaCl, pH 5.5. Product collection begins at 0.15 OD (A280, 1.0 cm path length) and collection ends at 50% of peak maximum. The eluate volume is approximately 5 CV. Residual product and contaminants are stripped from the column with 2 CV of 10 mM Tris, 1 M NaCl, pH 8.0 and discarded. The product obtained from the mixed mode column is filtered using a Millipore Opticap XL10, 0.22 µm Durapore capsule filter, (0.69 m$^2$). The product obtained from this step represents a recovery of about 70% of the Protein A material obtained in Step 2

Step 3B.

Mixed Mode Anion Exchange Chromatopgraphy. A 27.0 L (45 cm diameter×17 cm bed height) packed bed GE Healthcare Capto Adhere chromatography column is used to further purify the product obtained in step 3A above. Prior to use, the column is equilibrated with 2 CV of 25 mM Tris, pH 8.0 and sanitized with 2 CV of 0.1 N NaOH, 1 M NaCl and neutralized and equilibrated with 2 CV of 25 mM Tris, pH 8.0. Prior to product loading, the column is equilibrated with 3 CV of 10 mM Tris, pH 8.0. The Capto MMC pool from Step 3A above is adjusted to pH 8.1 with ~0.045 kg of 1 M Tris, pH 8.3 per kg of pool. The product from Step 3A above was diluted in-line 1:3.8 with WFI to adjust the conductivity to 12.0 mS/cm and pH 8.0. The resulting material is then applied to a column loading of up to 15 g/L media. The column is operated at a linear velocity of 170 cm/h to give a 6 minute residence time. After loading, the column is washed with 2 CV of 25 mM Tris, pH 8.0. The product is then eluted with a 10 CV gradient (20% to 90%) of 25 mM Tris, pH 8.0 to 10 mM Tris, 1 M NaCl, pH 8.0. Product collection is started at 0.15 OD (A280, 1.0 cm path length) and collection ended at 25% of peak maximum. The eluate volume is 4-6 CV. The eluted product is filtered using a commercially available capsule filter and then subjected in a known manner to viral filtration and tangential flow filtration steps. Overall product recovery from step 3B (including the final viral and tangential flow filtration steps) was approximately 68%. Product recovery measured before the filtration steps was about 75%. A schematic representation of HIC data obtained on eluation fractions from this step are representing in FIG. 12.

Analysis:

The final filtered product obtained in this example is found to have greater than about 90 wt % correctly folded etanercept as determined by HIC; less than 5 wt % incorrectly folded etanercept species as determined by HIC; less than about 3 wt % of dipped material by HIC analysis (believed to be fragments of etanercept in which the TNFR portion thereof has been truncated) and a combined amount of correctly and incorrectly folded etanercept of greater than 95 wt % as determined by size exclusion chromatography.

Analysis of Etanercept Formulations

A. Thermal Stability Storage

Following dialysis and concentration, samples of the etanercept formulations exemplified above were sterile filtered in a bio safety cabinet. Using sterilized pipettes and autoclaved pipette tips, samples of the etanercept formulations were transferred to pre-labeled and autoclaved 1 mL lyophilization vials. Vials were stoppered with sterile butyl stoppers and crimped with aluminum caps. All vials were then transferred to thermal stability ovens. Samples were subject to two thermal stability regimes: (1) two weeks at 40° C. and (2) four weeks at 25° C. Throughout this specification, these two temperature regimes are denoted "$T_1$," and $T_4$," respectively.

B. Size Exclusion Chromatography (SEC)

Etanercept formulations disclosed herein were analyzed using the well known technique of Size Exclusion Chromatography (SEC), a high-performance liquid chromatography method in which analytes are separated by size (see Rogner, M. (2000). Size Exclusion Chromatography. *Protein Liquid Chromatography*. M. Kastner. Amsterdam, Elsevier. 681: 89-145.). In order to evaluate thermal stability of the Etanercept samples described above, the samples were examined by a SEC method based on the literature (van Maarschalkerweerd, A., G. J. Wolbink, et al. (2011). "Comparison of analytical methods to detect instability of etanercept during thermal stress testing." *European Journal of Pharmaceutics and Biopharmaceutics* 78(2): 213-221.) The mobile phase buffer was prepared to contain 50 mM sodium phosphate monobasic monohydrate and 150 mM arginine. The pH was adjusted to 6.5 using 1 M HCl. All separations were performed using a Tosoh TSK-Gel SWxl 6 mm×4 cm guard column (cat no. 8543) attached linearly to a Tosoh TSK-Gel G4000 SWxl 7.8 mm×30 cm (cat. no. 8542). To perform a separation, the columns were brought to room temperature (23° C.) and equilibrated with mobile phase at a flow rate of 0.5 mL/min. 5 microliters of 50 mg/mL etanercept formulation were injected onto the column using an autosampler. The separation was accomplished over 30 minutes at a flow rate of 0.5 mL/minute. Column eluent was monitored at a wavelength of 280 nm during this time.

C. Integration of Size Exclusion Chromatography Chromatograms

All integration was performed using Chromeleon software (Dionex). Prior to integration, the SEC chromatogram for a buffer containing no etanercept was subtracted from all chromatograms. All integration was performed between retention times of 12 minutes and 26 minutes. Several parameters were used to define a peak. The minimum area for a detected peak was set to 0.05 mAu*min. The two-dimensional sensitivity for peak detection was set to 0.01 mAu and 75 seconds. Peak shoulders were added manually using a manual integration tool. All detected peaks were manually adjusted in two steps. First, peak baselines (the bottom boundary of the peak) were adjusted to horizontal. Secondly, the vertical positions of the peak baselines were adjusted to that of the chromatogram baseline. The chromatogram baseline value was defined as the signal in absence of analyte. The signal in absence of analyte was defined as the absorbance in mAu at 12 minutes retention time.

D. SEC Fractions of Etanercept Formulations

In the SEC analysis of etanercept formulations described above, three SEC chromatography fractions were identified and studied. The fractions that were analyzed were, in the order of elution from the SEC column: (1) a high molecular weight fraction representing aggregates of the intact etanercept TNFR:FC fusion protein likely assembled via non-covalent electrostatic attraction among intact etanercept molecules (hereinafter "aggregate(s)" or aggregate(s) content); (2) monomer content, representing the intact etanercept TNFR:Fc fusion protein (hereinafter referred to as "monomer" of "monomer content"); (3) a fraction likely representing one fragment or a population of fragments of the etanercept molecule in which one portion of the TNFR:molecule fusion protein has become cleaved from the monomer; in the loss of an arm of the Fab portion of the fusion protein at the hinge region of the molecule. The most common fragment or dipped species, as measured by SEC, is referred to as fragment 3. In conducting the SEC analysis, it will be observed that aggregates elute first, followed by monomer, followed by fragment 3.

The following tables shows the relative amounts of Aggregates, Monomer and fragment 3 determined by SEC analysis as described above.

TABLE 1

SEC ANALYSIS OF MONOMER

| | Formulation No. | | |
|---|---|---|---|
| | $t_0$ | $t_1$ | $t_2$ |
| Commercial Enbrel (comparative) [1:2] | 98.81 | 92.58 | 87.64 |
| 1:17 | 98.02 | 93.90 | 87.53 |
| 2:10 | 98.09 | — | 87.56 |
| 2:11 | 98.10 | — | 88.03 |
| 2:18 | 98.10 | — | 89.19 |
| 2:19 | 98.19 | — | 89.63 |

Note:
Amounts reported Tables I, II and III are percentages by weight
$T_0$ = formulation maintained at 5 C. and analyzed within 24 hours of creation.
$T_1$ = formulation stored for one week at 40° C.
$T_2$ = formulation stored for two weeks at 40 C.

TABLE II

SEC ANALYSIS OF AGGREGATES

| | Formulation No. | | |
|---|---|---|---|
| | $t_0$ | $t_1$ | $t_2$ |
| Commercial Enbrel (comparative) | 0.09 | 0.59 | 1.02 |
| 1:17 | 0.31 | 0.70 | 2.17 |
| 2:10 | 0.29 | — | 2.57 |
| 2:11 | 0.31 | — | 1.68 |
| 2:18 | 0.29 | — | 1.53 |
| 2:19 | 0.26 | — | 1.24 |

TABLE III

ANALYSIS OF FRAGMENT 3

| | Formulation No | | |
|---|---|---|---|
| | $t_0$ | $t_1$ | $t_2$ |
| Commercial Enbrel (comparative) | 0.00 | 3.30 | 6.29 |
| 1:17 | 0.00 | 2.33 | 4.10 |
| 2:10 | 0.00 | — | 5.10 |
| 2:11 | 0.00 | — | 5.68 |
| 2:18 | 0.00 | — | 4.24 |
| 2:19 | 0.00 | — | 4.34 |

HIC Analysis of Etanercept Formulations

HIC chromatography may be carried out in a manner known in the art and generally described in U.S. Pat. No. 7,294,481, incorporated herein by reference. Samples are evaluated at to (within 24 hours of preparation at 5° C.) and again after either two weeks of storage at 25° C. ($t_2$) or after 4 weeks of storage at 25° C. In the HIC chromatograms of the formulations of the present invention, Peak 1 in the HIC chromatogram is believed to be or include "Fragment 3", which is identified and quantified using SEC, as referenced above in the discussion of SEC data; Peak 2 is etanercept monomer as referenced above in the discussion of SEC data; and Peak 3 includes "Aggregate(s)" as referenced above in the discussion of SEC data. It should further be understood that the terms "peak 1", "peak 2" and "peak 3 as used here also constitute a reference to the HIC peak 1, peak 2 and peak 3 referred to and disclosed in FIG. 4 of U.S. Pat. No. 7,294,481 incorporated herein by reference.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of reducing formation of etanercept aggregates or fragments in an aqueous composition containing 25 to 75 mg/ml etanercept, the method comprising combining
    a) etanercept,
    b) buffer, and
    c) stabilizer comprising 6 to 10 weight % (wt. %) xylitol, wherein the aqueous composition has a pH of 6.0 to 6.6, or a pH within 10 percent of 6.0 and 6.6, wherein the aqueous composition is free or essentially free of arginine, thereby preparing the aqueous composition.

2. The method of claim 1, wherein the aqueous composition comprises 10 wt. % xylitol.

3. The method of claim 1, wherein the aqueous composition comprises 50 to 75 mg/ml of etanercept.

4. The method of claim 1, wherein the aqueous composition comprises 50 mg/ml or a concentration within 10 percent of 50 mg/ml of etanercept.

5. The method of claim 1, further comprising adding one or more additional components selected from a buffer, a tonicity modifier, and an excipient to the aqueous composition.

6. The method of claim 1, further comprising adding one or more additional components selected from meglumine, mannosylglycerate, mannosyllactate, mannosylglycolate, and diglycerolphosphate to the aqueous composition.

7. The method of claim 1, wherein the aqueous composition has osmolality of 180 to 420 milliosmoles or an osmolality within 10 percent of 180 to 420 milliosmoles.

8. The method of claim 1, further comprising filling the aqueous composition in a device suitable for administration to a subject as a single dose.

9. The method of claim 8, wherein the dose contains 10 to 100 mg/dose etanercept.

10. The method of claim 1, wherein the aqueous composition elicits long term storage stability as characterized by SEC (size exclusion chromatography) analysis at $T_2$ of monomer content greater than 90%.

11. The method of claim 1, wherein the aqueous composition has no more than, on average, 10,000 subvisible particles per ml having a size greater than 5 µm.

12. The method of claim 1, wherein the aqueous composition elicits long term storage stability as characterized by at least one of:
    (a) SEC (Size Exclusion Chromatography) analysis at $T_2$ of monomer content greater than 80 or 90%; aggregates content of less than 3 wt. %; and fragment 3 content less than 5 or 6 wt. %; or
    (b) HIC (Hydrophobic Interaction Chromatography) analysis at $T_2$ wherein the amount of the composition represented by peak 1 of the HIC chromatogram is less than 3 wt. %; the amount of the composition represented by peak 2 of the HIC chromatogram is greater than 80 wt. %; and the amount of the composition represented by peak 3 of the HIC chromatogram is less than 20 wt. %.

13. The method of claim 12, wherein the aqueous composition has an HIC analysis at $T_2$ wherein the amount of the composition represented by peak 1 of the HIC chromatogram is less than 1 wt. %; the amount of the composition represented by peak 2 of the HIC chromatogram is greater than 95 wt. %; and the amount of the composition represented by peak 3 of the HIC chromatogram is less than 3 wt. %.

14. The method of claim 1, wherein the aqueous composition elicits long term storage stability as characterized by an SEC (Size Exclusion Chromatography) analysis at $T_2$ of greater than 80 wt. % monomer content; less than 3 wt. % aggregates content; and less than 6 wt. % fragment 3 content.

15. A vial, syringe, or injector pen containing a aqueous composition comprising 25 to 75 mg/ml etanercept and 6 to 10 wt. % xylitol in an aqueous pharmaceutical composition having a pH of 6.0 to 6.6 or a pH within 10 percent of 6.0 and 6.6, wherein the composition is free or essentially free of arginine.

* * * * *